US00PP09183P

United States Patent [19]

Van Der Meer

[11] Patent Number: Plant 9,183

[45] Date of Patent: Jul. 4, 1995

[54] HYBRID TEA ROSE PLANT NAMED 'SELHAFNIUM'

[75] Inventor: Peter J. A. Van Der Meer, Carlsbad, Calif.

[73] Assignee: Terra Nigra B.V., De Kwakel, Netherlands

[21] Appl. No.: 105,358

[22] Filed: Aug. 11, 1993

[30] Foreign Application Priority Data

Dec. 15, 1992 [NL] Netherlands ..... R001913

[51] Int. Cl.[6] ..... A01H 5/00

[52] U.S. Cl. ..... Plt./15

[58] Field of Search ..... Plt. 15, 11

[56] References Cited

U.S. PATENT DOCUMENTS

P.P. 1,712 5/1958 Combe ..... Plt./11

P.P. 4,063 6/1977 McGredy, IV ..... Plt./15

OTHER PUBLICATIONS

Modern Roses 9, 1986, The American Rose Society. pp. 332–333.

*Primary Examiner*—Howard J. Locker

[57] ABSTRACT

A new rose variety of the Hybrid Tea class, characterized by its medium to large sized yellow-cream colored flowers having a mild, honey-like fragrance, said flowers being borne singly on strong, upright stems on a sturdy bush of medium height.

2 Drawing Sheets

BACKGROUND OF THE INVENTION

The present invention relates to a new and distinct variety of rose plant of the Hybrid Tea class, which was originated by me by crossing the variety "Tanja" with an unnamed (SR 85.085) and unpatented seedling.

"Tanja" differs from "Selhafnium" by its orange flower color, smaller flower size, and shorter stems.

The primary objective of this breeding was to obtain a new rose variety comparable to that of "Tanja", but with a larger flower and stronger stems. While the results achieved a distinct yellow Hybrid Tea rose of large size, the new variety did not otherwise correspond to the characteristics of "Tanja", but nevertheless, achieved a new and distinct combination of characteristics which is desirable and attractive, as well as different from anything heretofore available, as evidenced by the following characteristics which are outstanding in the new variety:

(1) a large yellow flower (2) rapid flowering cycles (3) distinctive fragrance (4) a vigorous upright plant of medium height (5) a plant which has many thorns on the stems and many little prickles on the peduncle The foregoing characteristics and distinctions definitely differentiate the new variety from its parents, as well as from all other varieties of which I am aware, and asexual reproduction of the new variety by cuttings, grafting or tissue culture as performed in a greenhouse in De Kwakel, the Netherlands, shows that these and all other characteristics and distinctions come true to form and are established and transmitted through succeeding propagations.

BRIEF DESCRIPTION OF THE DRAWINGS

The new variety of rose plant is illustrated by the accompanying photographic illustrations, of which:

Sheet 1 shows a full face view of the flower and

Sheet 2 shows typical specimens of the vegetative growth and flowers of the new variety in different stages of development. The color renditions are as nearly true as as it is possible to make same in color illustrations of this character by conventional photographic procedures.

The following is a detailed description of this new variety, with color terminology in accordance with The Royal Horticultural Society Colour Chart (R.H.S.C.C.). The terminology used in the color description herein refers to plate numbers in the aforementioned color chart e.g. "53A" is plate "53A" of The Royal Horticultural Society Colour Chart.

Parentage: Seedling.

*Seed parent.*—"Tanja".

Pollen parent.—Unnamed seedling (SR 85.085).

Classification:

*Botanic.*—Hybrid Tea.

*Commercial.*—Hybrid Tea.

BOTANICAL DESCRIPTION OF THE PLANT

Flower (Observations made from specimens grown in a greenhouse at De Kwakel, the Netherlands)

Blooming habit of Selhafnium: Recurrent-continuous.

A. Bud:

(1) *Size.*—Large. Diameter 2.0–2.5 cm. Length 3.0–3.5 cm.

(2) *Form.*—Egg shaped (oval, pointed;) is not affected by wet or hot weather.

(3) *Color.*—When the sepals first divide, the color of the outside is yellow 154C with some green 139B and pink edges 39C.

(4) *Sepals.*—Slightly branched, stand up when petals begin to unfurl. Color: inside: green 138B. outside: green 143B.

(5) *Calyx.*—Color: green 142B. Shape: pear. Size: broad. Aspect: Smooth. Odor when rubbed: weak.

(6) *Peduncle.*—Length: long 10 cm. Aspect: prickled. Strength: good. Color: green 144A.

(7) *Opening.*—Opens up well; is not affected by adverse weather.

B. Bloom:

(1) *Size.*—Large: when fully expanded about 10 cm in diameter with a depth of about 4 cm.

(2) *Borne.*—Single.

(3) *Stems.*—Length: long. Strength: strong.

(4) *Form (when first open).*—Cup-form. Permanence: will flatten when aging.

(5) *Petalage.*—Number of petals: 30–35.

(6) *Color.*—Center of flower: yellow (8B-C). Outer petals: yellow (8D). Base of petals: yellow (8B). Inside of petals: yellow (8B-C). Reverse of petals: yellow (8D). General tonality: yellow (8B-C).

(7) *Discoloration.*—General tonality at end of first day: yellow (8B-C). Second day: same color. Third day: fading to white.

C. Petals:

(1) *Texture.*—Leathery; not affected by wet or hot weather.

(2) *Appearance.*—Inside: shiny. Outside: satiny.

(3) *Form.*—Round shaped.

(4) *Arrangement.*—Regular.

(5) *Petaloids in center.*—Few; small.

(6) *Persistence.*—Drop off cleanly.

(7) *Fragrance.*—Weak; honey-like scent.

(8) *Lasting quality.*—On the plant — long. As cut flower — long (more than 12 days).

Reproductive Organs

Stamens, anthers:

*Size.*—Medium; regularly arranged around styles, average number about 175.

*Color.*—Yellow.

Stamens, filaments (threads): long, average about 10 to 15 mm in length.

*Color.*—Yellow.

Pollen:

*Color.*—Yellow.

Styles: Bunched; uneven length; medium (about 5–6 mm) length; thin.

Stigmas:

*Color.*—Yellow.

Ovaries: All enclosed in calyx; round shaped.

Hips seeds: None observed.

Resistancy: Normal resistance against mildew, white fly, Californian thrips; More sensitive to red spider mixes.

Plant

Form: Bushy and upright.

Growth: Vigorous: upright; medium height; average height is 80–100 cm.

(1) *Size.*—Average.

(2) *Quantity.*—Abundant.

(3) *Color.*—New foliage: upper side — green 137A. under side — green 191B. Old foliage: under side — green 191B. upper side — green 137B.

(4) *Shape.*—Oval pointed.

(5) *Texture.*—Upper side — smooth, dull. Under side — smooth, dull.

(6) *Ribs and veins.*—Ordinary.

(7) *Edge.*—Serrated, saw toothed.

(8) *Serration.*—Single.

(9) *Leaf stem.*—Color: green 143A. Under side: smooth; underside may have up to about 4 small bent prickles about 5 mm in length; some hairs may appear on the edge of the upper side.

(10) *Stipules.*—Medium length, smooth.

Wood:

*New wood.*—Color: bronze. Bark: smooth.

*Old wood.*—Color: green. Bark: smooth.

Thorns:

*Quantity.*—On main stalks from base: few, about 4–5 per 10 cm stem length. On laterals from stalk: few. Form: concave. Length: large. Hooked: downward. Color (when young): green-bronze. Position: irregular.

Prickles:

*Quantity.*—On main stalks: few. On laterals: few.

Short needles:

*Quantity.*—On main stalks: many. On laterals: many.

I claim:

1. A new and distinct variety of rose plant of the Hybrid Tea class, substantially as herein shown and described characterized particularly as to novelty by its medium-large yellow flowers, borne singly on strong, upright stems on a sturdy bush of medium height.

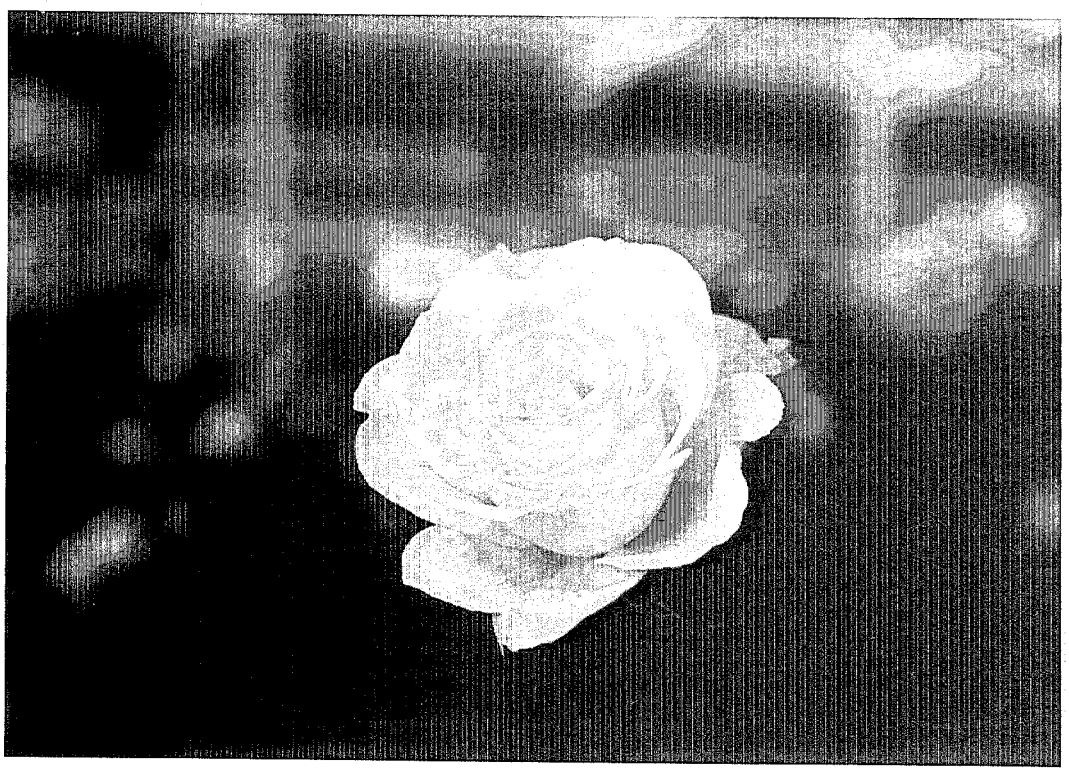

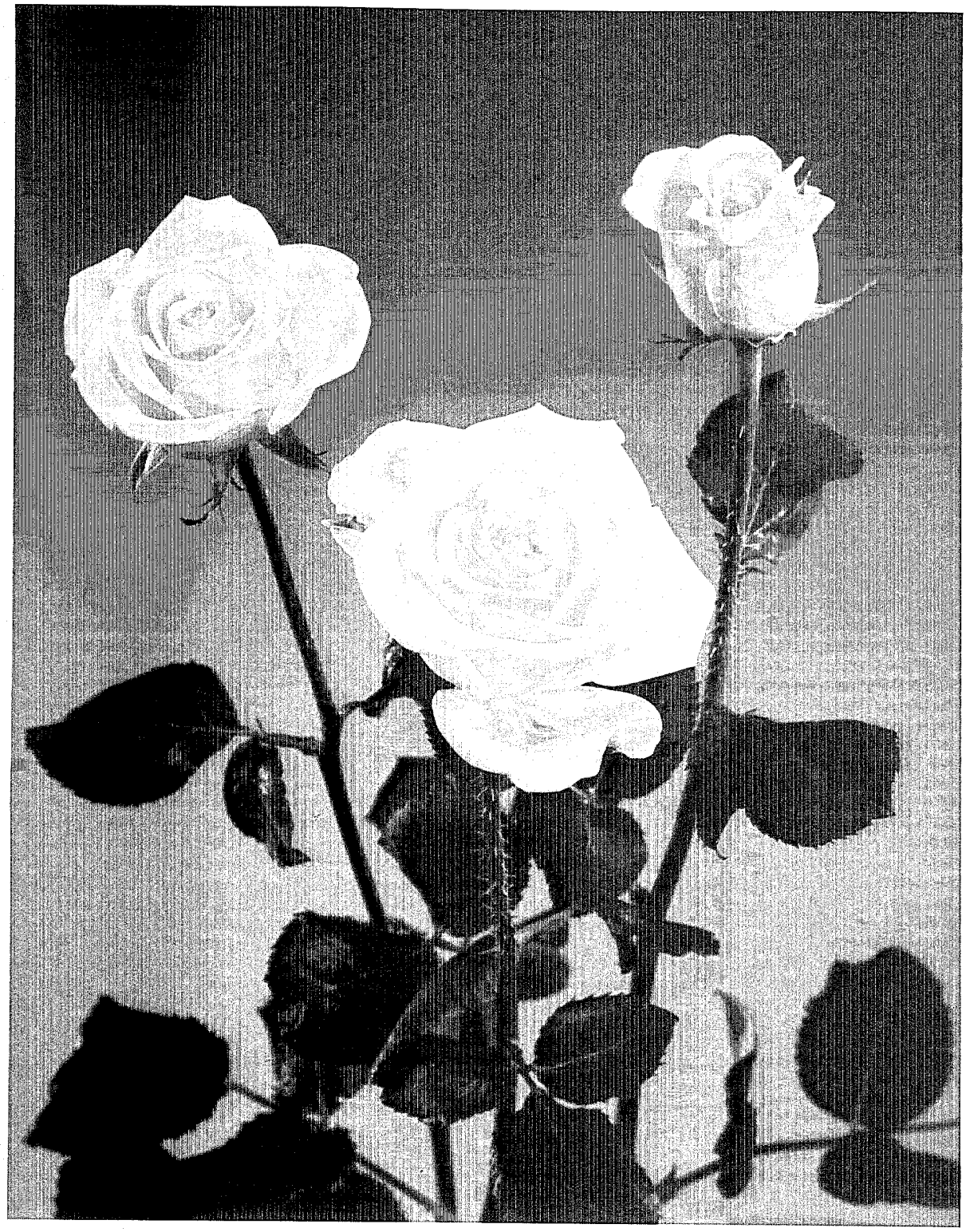

* * * * *